US006224521B1

(12) United States Patent
Foucault

(10) Patent No.: US 6,224,521 B1
(45) Date of Patent: May 1, 2001

(54) ORTHOPEDIC EXERCISER

(75) Inventor: André Foucault, Victoriaville (CA)

(73) Assignee: Mission Santé Bois-Francs Inc., Victoriaville (CA)

( * ) Notice: Subject to any disclaimer, the term of this patent is extended or adjusted under 35 U.S.C. 154(b) by 0 days.

(21) Appl. No.: 09/326,683

(22) Filed: Jun. 7, 1999

(30) Foreign Application Priority Data

Jun. 8, 1998 (CA) .......... 2239144

(51) Int. Cl.[7] .......... A63B 21/008; A61H 1/00; A61F 5/00

(52) U.S. Cl. .......... 482/112; 601/34; 602/23; 602/16

(58) Field of Search .......... 601/5, 33–35; 482/101, 112, 113, 135; 602/5, 16, 23, 32, 33, 35, 36, 38; 5/624, 648–651

(56) References Cited

U.S. PATENT DOCUMENTS

| | | | | |
|---|---|---|---|---|
| 3,976,057 | * | 8/1976 | Barclay | 601/34 |
| 4,050,455 | * | 9/1977 | Smith | 602/16 |
| 4,229,001 | * | 10/1980 | Roman | 482/79 |
| 4,323,060 | * | 4/1982 | Pecheux | 601/34 X |
| 4,492,222 | | 1/1985 | Hajianpour | 128/25 R |
| 4,558,692 | | 12/1985 | Greiner | 128/25 R |
| 4,603,687 | | 8/1986 | Greenwood | 128/25 R |
| 4,604,997 | * | 8/1986 | De Bastiani et al. | 602/16 X |
| 4,782,827 | | 11/1988 | Paratte | 128/80 R |
| 4,834,073 | * | 5/1989 | Bledsoe | 601/34 |
| 4,844,454 | | 7/1989 | Rogers | 272/126 |
| 4,922,892 | | 5/1990 | Akcelrod et al. | 128/25 R |
| 5,031,905 | * | 7/1991 | Walsh | 482/112 |
| 5,074,549 | | 12/1991 | Harvey | 272/93 |
| 5,122,106 | | 6/1992 | Atwood et al. | 482/131 |
| 5,239,987 | * | 8/1993 | Kaiser et al. | 601/34 |
| 5,273,520 | * | 12/1993 | Rebmann | 601/34 X |
| 5,333,604 | | 8/1994 | Green et al. | 601/33 |
| 5,423,862 | | 6/1995 | Clarke et al. | 606/242 |
| 5,472,410 | | 12/1995 | Hamersly | 602/16 |
| 5,509,894 | | 4/1996 | Mason et al. | 601/34 |
| 5,529,573 | | 6/1996 | Kelly et al. | 601/34 |
| 5,571,078 | * | 11/1996 | Malecicz | 602/16 X |
| 5,647,823 | | 7/1997 | Spence | 482/91 |
| 5,662,596 | * | 9/1997 | Young | 602/16 X |
| B1 4,323,060 | * | 9/1985 | Pecheux | 601/34 X |

* cited by examiner

*Primary Examiner*—Mickey Yu
*Assistant Examiner*—Denise Pothier
(74) *Attorney, Agent, or Firm*—Robic

(57) ABSTRACT

An orthopedic apparatus for rehabilitation or healing of a knee or the muscles of a leg. The apparatus has a dynamic adjustment mechanism allowing the execution of exercise of different degrees of tension without running the risk of injuring the knee by applying unnecessary or excessive amount of tension on the knee. The dynamic adjustment mechanism is designed to keep the eccentricity of the rotational axes of the leg support member and the leg nil. The orthopedic apparatus may also include a resistance or assistance mechanism for adjusting different degrees of tension during extension and flexion of the leg in order to gain either range of movement or strength. This specially designed mechanism provides a linear type resistance or assistance, which is invariable during the whole range of movement. This particular resistance, applied on the plantar foot, reproduces normal bio-mechanical stress on the lower limb. The exerciser may further include a blocking mechanism for allowing instant pause and prevents reversal of the movement during the exercise. Finally, the exerciser may still include a static adjustment mechanism for adjusting the leg support member to a predetermined length.

9 Claims, 9 Drawing Sheets

ORTHOPEDIC EXERCISER

FIELD OF THE INVENTION

The present invention relates to orthopedic exerciser for therapy, post-surgery rehabilitation or healing of a knee or the muscles of a leg.

BACKGROUND OF THE INVENTION

Various surgical techniques have been known since the early 80's for the treatment of articular disorders. The complete replacement of an articulation of the knee is commonly practised nowadays. Rehabilitation of operated knees has become needy and different new options have been developed.

Several exercises have been proposed in different rehabilitation programs. They all aim to recover the knee to the normal articular mobility to disappearance of pain, to functional proprioception and to normal muscular function.

Currently there are four main type of exercises to aid in the rehabilitation of the knee, namely, passive, active assisted, active and "against resistance". The condition of the patient may determine the type of exercise to be practised. Traditionally, passive movement is used to allow a gain of amplitude in the articular movement by diminishing inflammatory reactions, pain or muscular cramps. The exercises requiring active muscular movement usually follow after disappearance of the pain.

A CPM (Continuous Passive Motion) apparatus is a commonly used apparatus in knee rehabilitation. This apparatus allows execution of passive flexion and extension movement during a long period of time and without effort from the patient. CPM may be very efficient in terms of reducing pain in the knee or leg in post-surgery rehabilitation treatment, reducing hospitalization time and reducing a number of complications that may occur during the rehabilitation period. However, CPM does not replace functional activity and active movement.

Once the patient is able to execute contraction of muscles without excessive pain, which may be very soon, active assisted movement of the leg is practised. It is then possible to gain range of movement (ROM) without any motorised assistance. In our experience, simple mechanical assistance in either flexion or extension movement allows greater benefits than a motorised device. Assistive active devices are necessary when muscles are not functional enough to move the joint in the devised range.

The next step to undertake for allowing full recovery of the knee or leg, that is for allowing their proper functioning, is to execute "against resistance" exercises. Actually, this type of exercise allows restoration of proprioceptive neuromuscular facilitation. It is known that rehabilitation of a muscle and maintenance of development of the muscle tone is possible from the different reflex mechanisms generated by stretching of the muscle which results from the physical action of the muscle itself.

Different publications and patents disclose an apparatus allowing application of resistance during extension of the knee through a movement of an arc of a circle. The thigh is maintained still or partially still, whether the patient is sitting or lying down. Other apparatuses comprise a simple support for receiving a thigh and a resistance device which may be a bag of sand attached to the foot. In other instances, the resistance device may be an elastic band. In all cases, the foot usually lacks proper support and the resistance is exercised on the wrong portion of the leg, for instance, in the lower portion, i.e. the shank. All these apparatus challenge the muscles in a wrong bio-mechanical way, and may damage the knee. These old-fashioned exercises are so called "open circuit" type.

Obviously, it is important to provide an apparatus that will allow execution of the exercise without causing tension on the knee. Recent data have shown the best benefits of a new approach.

SUMMARY OF THE INVENTION

It is an object of the present invention to provide an apparatus allowing execution of a wide range of exercises of a leg without causing excessive tension on the knee.

It is a further object of the present invention to provide an apparatus allowing execution of a complete combination of exercise that will result in the complete recovery of the joint of exercises, performed in a normal functional way, by applying resistance or assistance on the plantar part of the foot. These exercises are called "closed circuit exercises", or "closed kinetic chain" exercises. They challenge muscles and articulation in the proper bio-mechanical way. One important feature of the apparatus according to the invention lies in the use of the same mechanical device i.e. a pair of pistons, to either assist active still movement, to gain range or resist active movement to gain strength, in opposite directions of course, but in both flexion and extension.

The apparatus according to the present invention comprises a main frame, and a leg support member slidably mounted on the main frame. The support member comprises a first portion designed to receive a thigh, a second portion designed to receive a shank and a third portion designed to receive a foot. The first and second portions each comprise two opposite side edges defining the width of the support member. The first and second portions are pivotably connected to each other and form a first rotation axis for allowing flexion of a knee about a second rotational axis. The apparatus is characterized in that it comprises:

- a dynamic adjustment mechanism for minimizing tension on the knee during extension or flexion of the leg, said mechanism allowing no eccentricity between the first and second rotational axes.

The first and second portions are pivotally connected so that when the leg is flexed and extended, the first and second axes are substantially coincident throughout the range of motion.

As mentioned above, one advantage of having such a dynamic adjustment mechanism is to allow proper resistive or assistive exercise of the leg without running the risk of further injuring the knee.

DETAILED DESCRIPTION OF THE INVENTION

Figure 1:
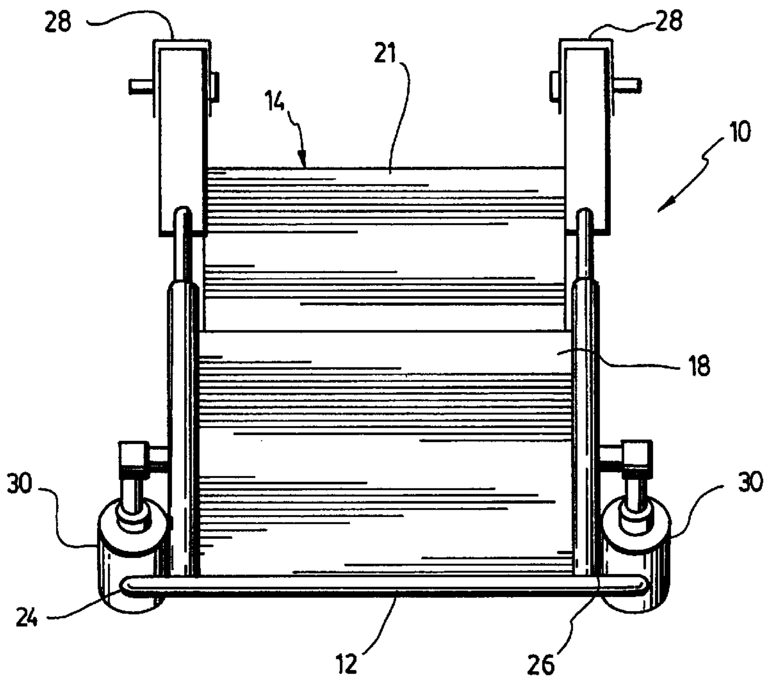
FIG. 1, is a front view of the orthopedic apparatus according to a preferred embodiment of the present invention.
Figure 2:
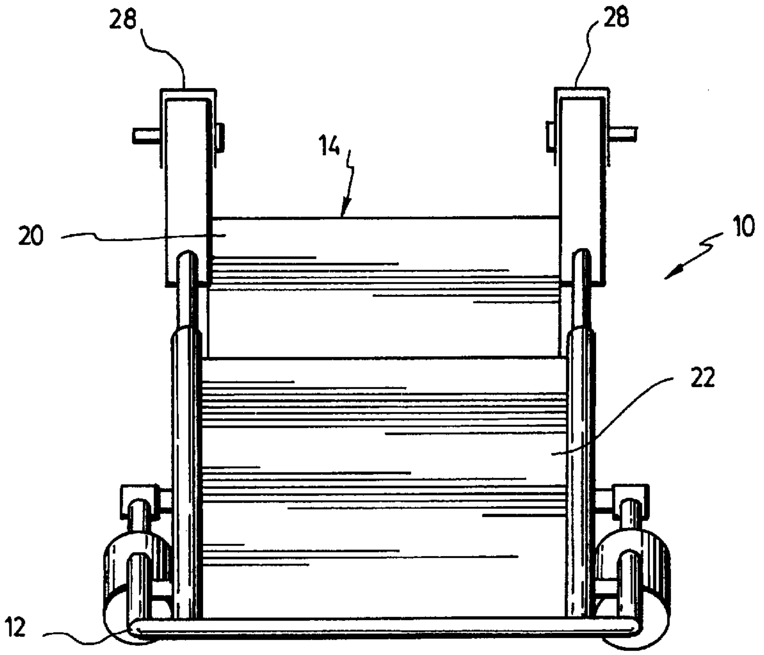
FIG. 2, is a rear view of the orthopedic apparatus of FIG. 1.

As can be seen in FIGS. 1 to 6, the orthopedic apparatus (10) according to the present invention comprises a main frame (12) which has a pair of rails (16) . The main frame is designed to receive a leg support member (14). The leg support member (14) has two opposite ends, one of which is fixedly secured to an end on the leg support member (14), the other opposite end being slidably secured on the rails (16) of the main frame (12).

The leg support member (14) can be divided into three portions. A first portion (18) is designed to receive a thigh, a second portion (20) is adapted to receive a shank and a third portion (22) adapted to receive a foot, so as to furnish a proper support for the whole leg. The first and second portions (18, 20) are pivotally connected about a second rotational axis so to allow flexion and extension of the leg about a first rotational axis.

The width of the leg support member (14) is defined by two opposite side edges (24, 26).

Figure 7:
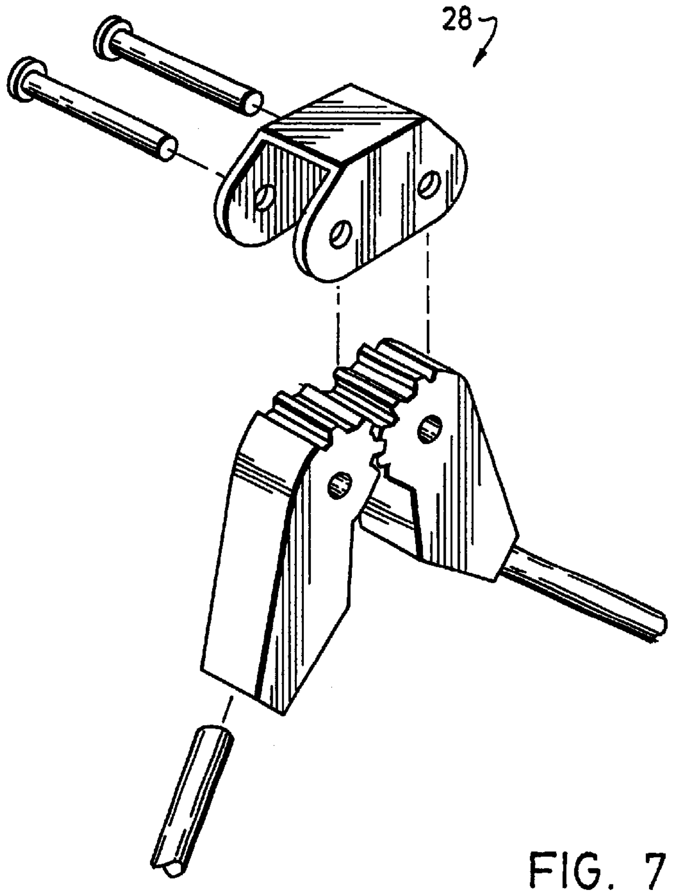
FIG. 7 is an exploded view of a dynamic adjustment mechanism according to a preferred embodiment of the orthopedic apparatus of the present invention.

The orthopedic apparatus (10) comprises a dynamic adjustment mechanism, shown on FIG. 7 for minimizing tension on the knee during extension and flexion of the leg. The dynamic adjustment mechanism allow tension-free movement of the knee by always maintaining the eccentricity between the rotational angle of the leg support member (14) and the knee nil. The dynamic adjustment mechanism may be any mechanism that yields such result. One of the main purposes of the dynamic adjustment mechanism is to prevent friction between the leg and the apparatus during flexion and extension, due mostly to the accumulation of flesh directly under the knee, and due partly to an additional movement of rotation and translation of the shank with respect to the thigh.

In a preferred embodiment, the dynamic adjustment mechanism consists of an indented hinge (28).

The indented hinge (28) is designed to allow a dynamic adjustment of the leg support member (14) relative to the length of the leg during movement of same, that is during flexion and extension. The rotational axis of the indented hinge (28) follows the rotational axis of the knee so to minimize the eccentricity between the leg and the hinge (28). The indented hinge (28) pivotally connects the first and second portions (18, 20) of the leg support member (14) so that when the first and second portions (18, 20) are brought up to form a horizontal plane, the rotational axis of the hinge (28) is protruding from the plane. As a result when the leg is at the extended or flexed position, the rotational axis of the hinge (28) and that of the leg coincide. In other words, the proposed mechanism follows closely the actual movement of the rotational axis of the knee either during extension or flexion of the leg, resulting in almost complete absence of friction between the leg of the patient and the portions of the leg support member (14) all the while keeping the leg of the patient uniformly and properly supported on the leg support member (14).

Figure 13A:
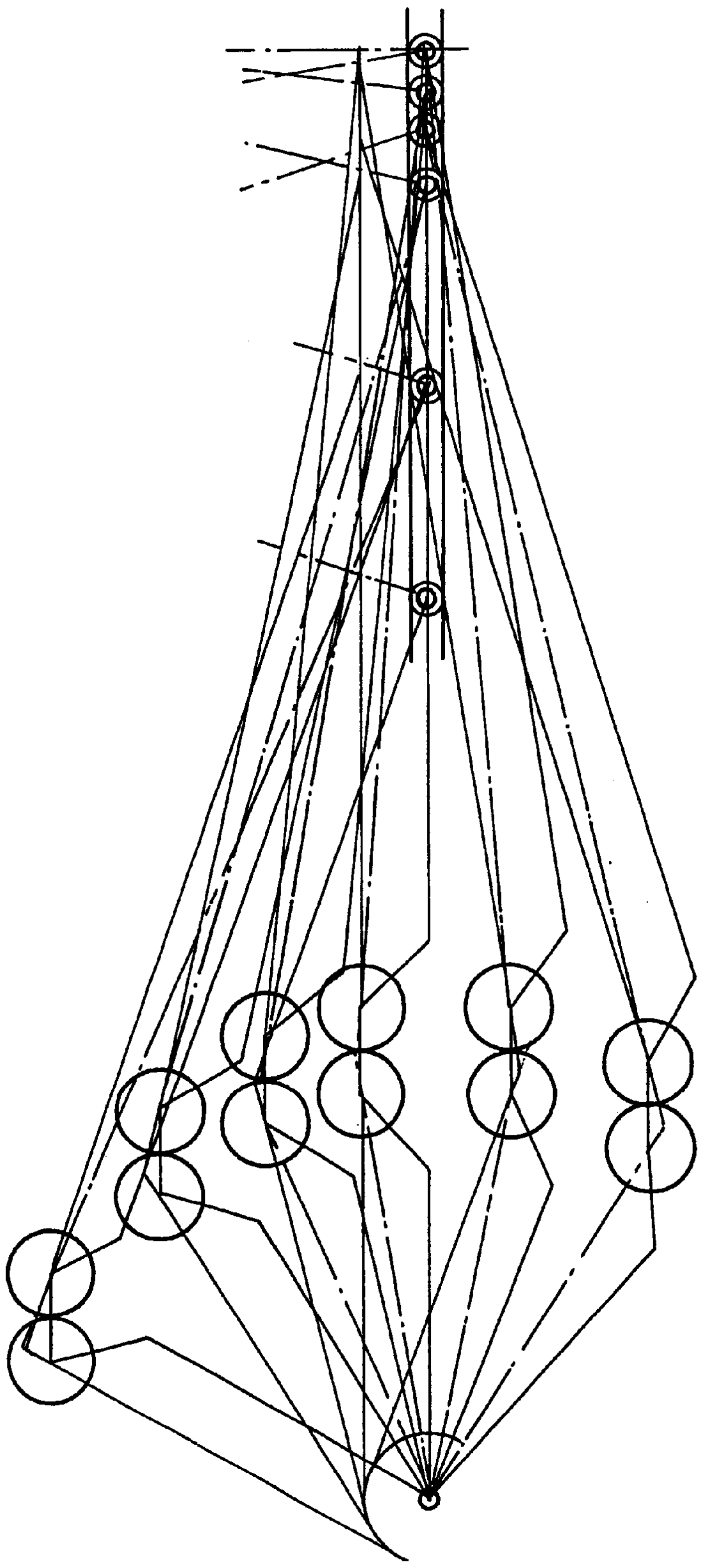
FIGS. 13*a, b, c* and *d* are schematic representations of the alignment between the first and second axes of rotation throughout the range of motion for legs of different lengths.
Figure 13B:
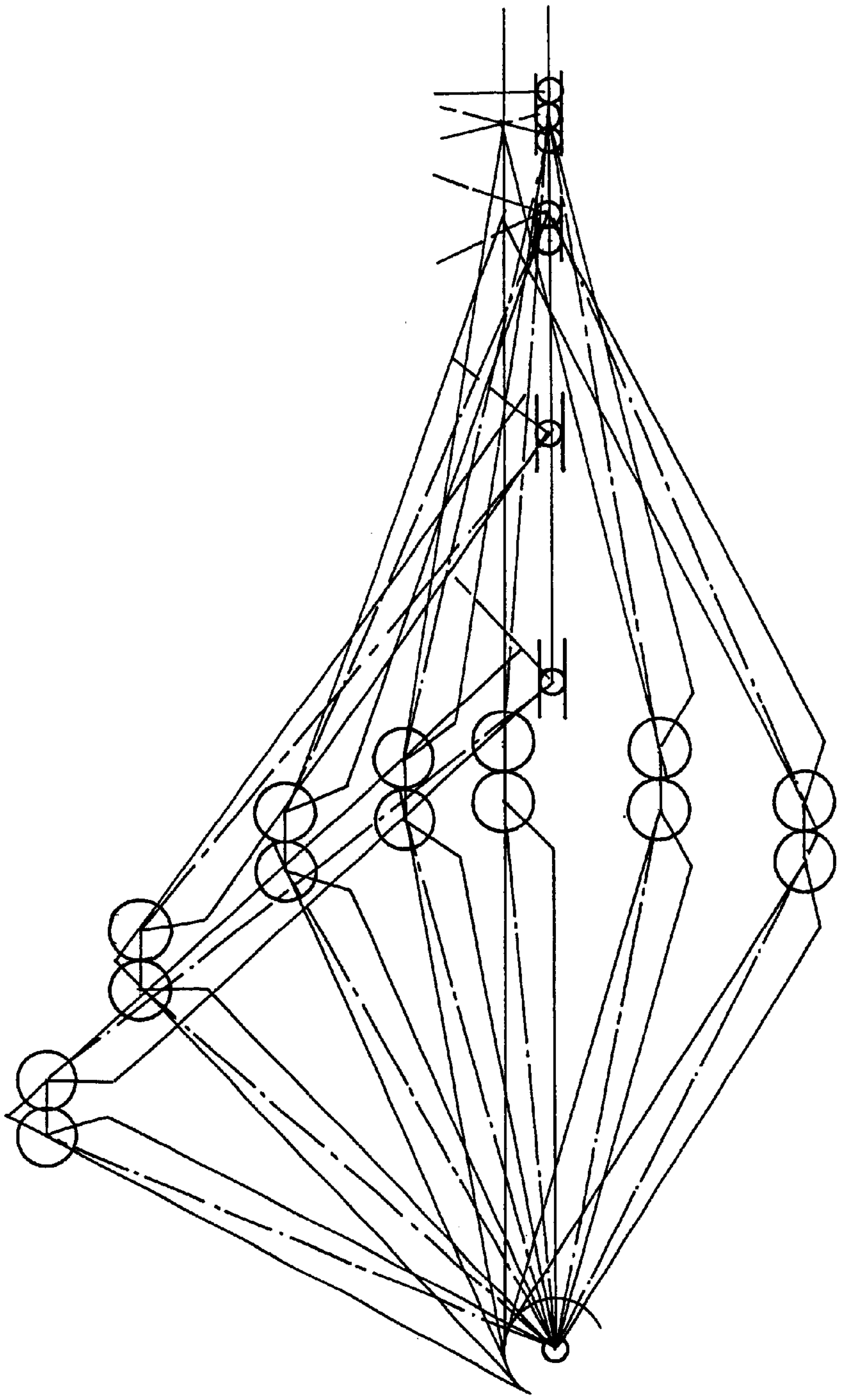
Figure 13C:
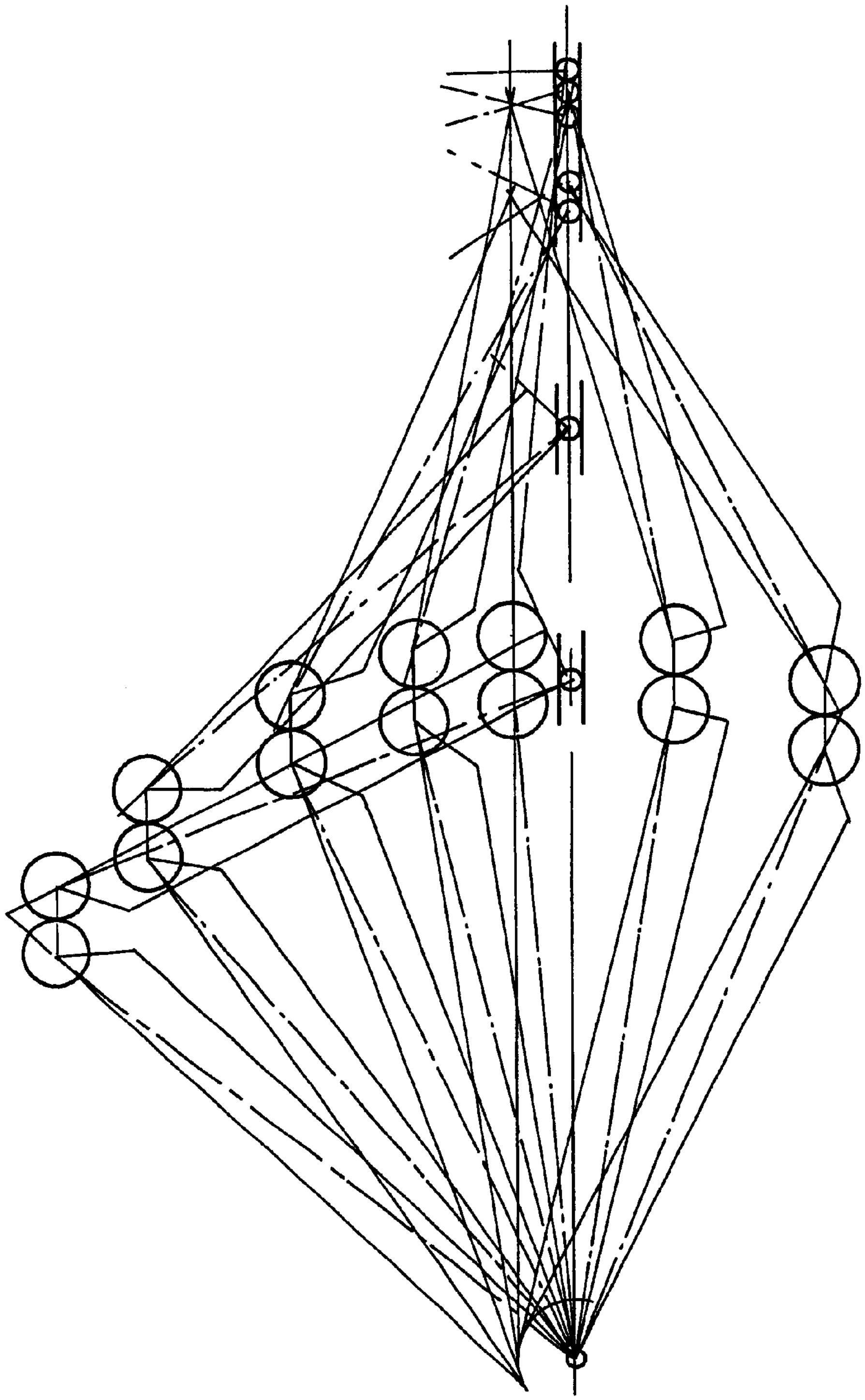
Figure 13D:
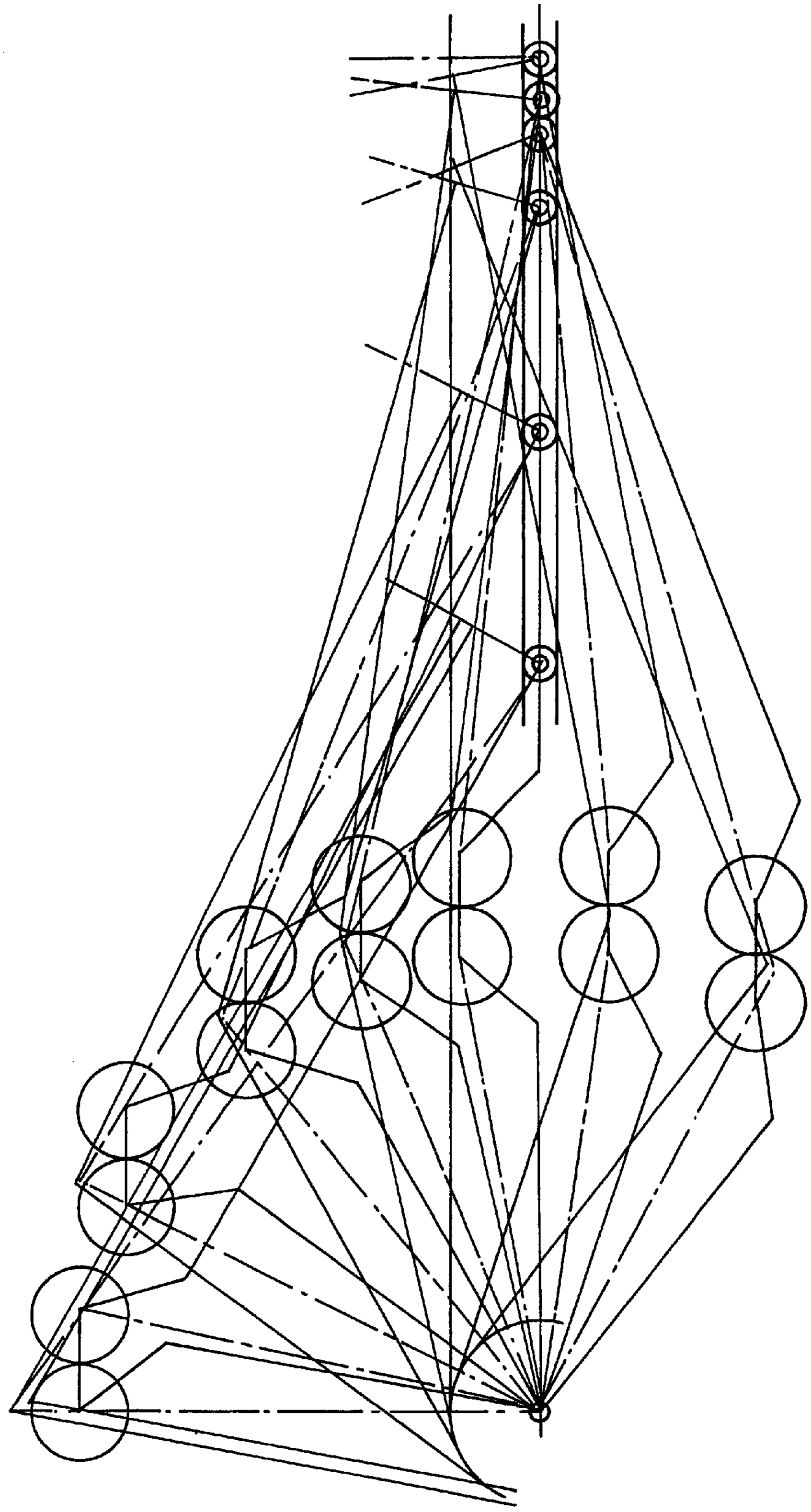

Hence, the main purpose of a dynamic adjustment mechanism is to provide a hinge (28) having a rotational axis adjacent to the one of the leg so that the eccentricity between the knee and hinge is insignificant, thereby significantly reducing the tension that may be applied on the knee during the movement of the leg. The hinge is different from prior art machines in that its axis of rotation, when the leg is flexed, coincides with the axis of rotation of the knee throughout the range of motion, as best seen in FIGS. 13*a, b, c* and *d.* In these figures, the intersections of the dashed lines corresponds to the instantaneous center of rotation of the indented hinge, whereas the intersection of the full lines corresponds to the instantaneous center of rotation of the knee of a patient. The distance between the two points is minimal, so that the first and second axes of rotation are substantially coincident throughout the range of motion, for legs of various lengths. One should note that the lengths stated in FIGS. 13*a, b, c, d* are: for the thigh, the distance between the pubic area (lower part) and the knee, and for the shank, the distance between the knee and the bottom of the heel. One will note a slight degradation when at maximal flexion, which is due to mechanical constraints. Consequently, the apparatus according to the present invention follows very closely the real movement of the knee during flexion and extension, and results in very little friction between the legs of a patient and the apparatus, with constant and uniform contact of the heel on the third portion (22) of the apparatus. One will also note that the figures show an unrealistic movement below the plane of the apparatus, and these are included in the figures as the representations are based on mathematical modelling.

Figure 3:
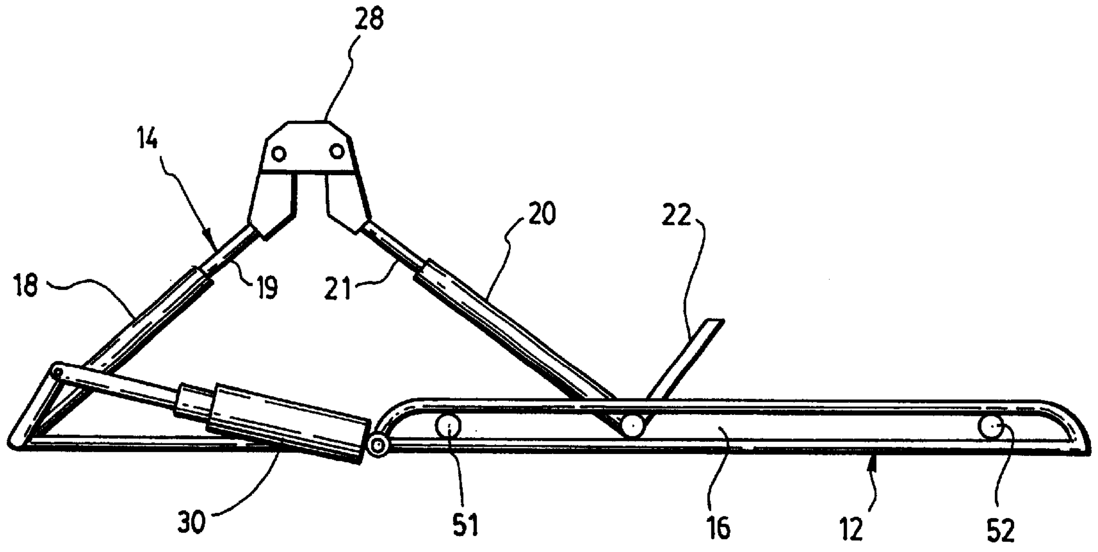
FIG. 3 is a side view of the orthopedic apparatus of FIG. 1.
Figure 4:
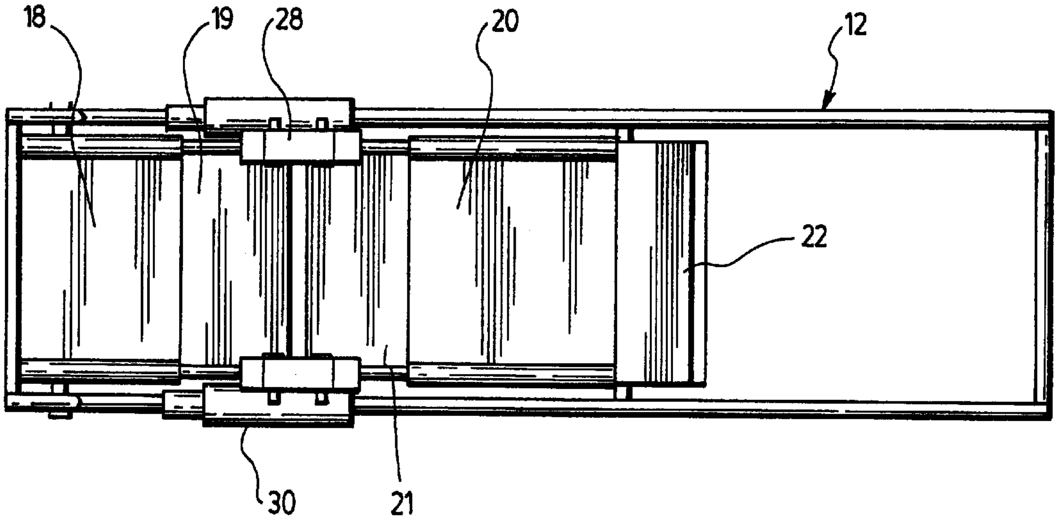
FIG. 4 is a top view of the orthopedic apparatus of FIG. 1.
Figure 5:
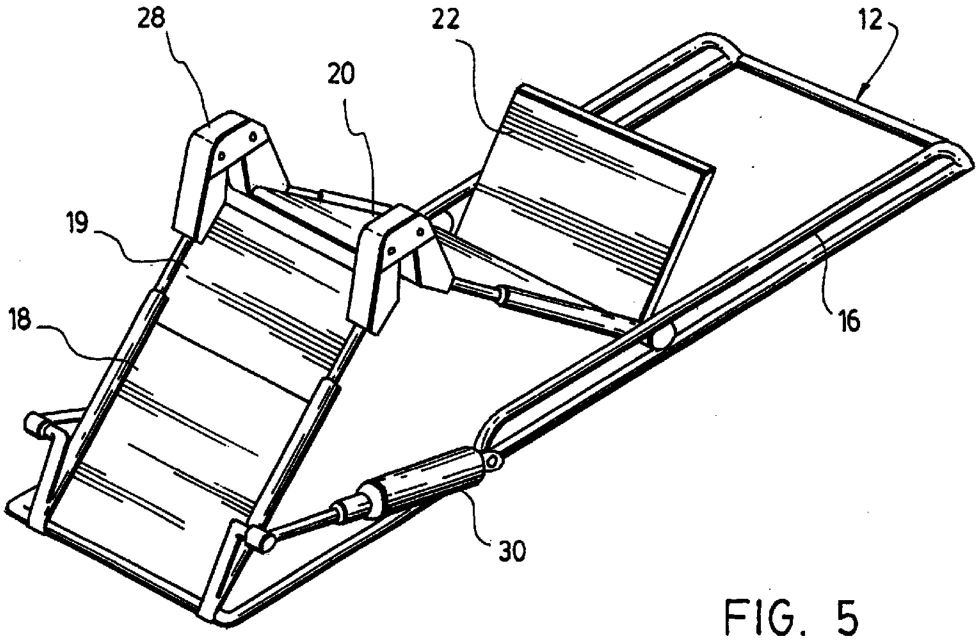
FIG. 5 is a perspective view from the back of the orthopedic apparatus of FIG. 1.
Figure 6:
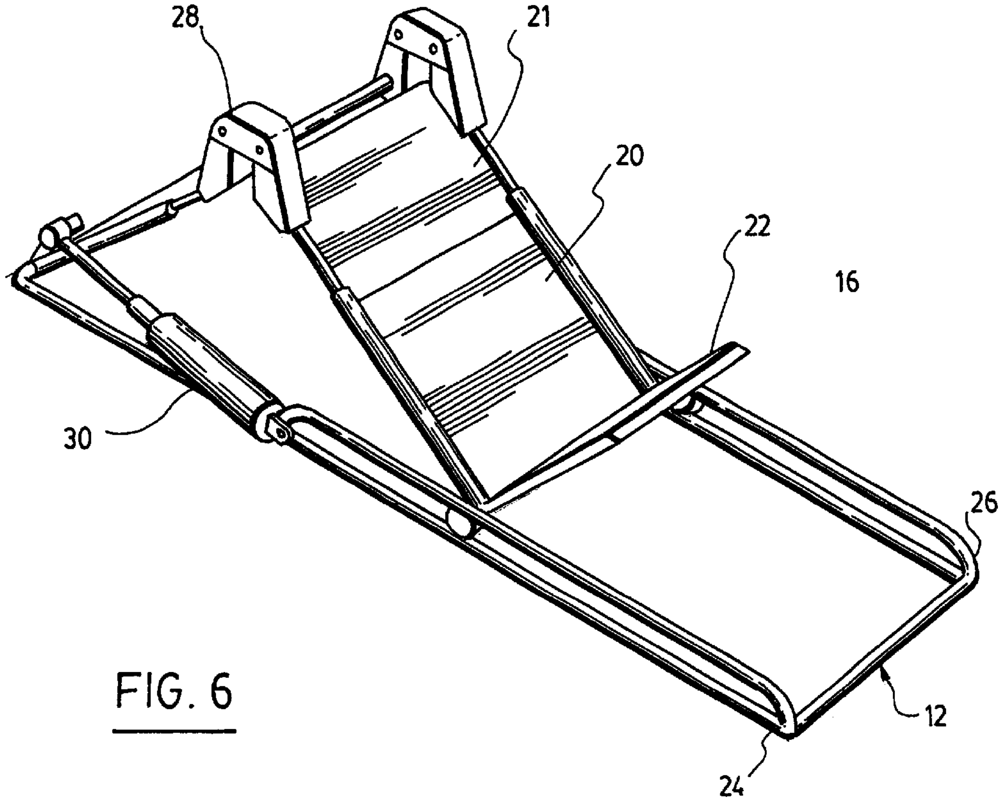
FIG. 6 is a perspective view from the front of the orthopedic apparatus of FIG. 1.

The orthopedic apparatus also preferably comprises a resistance mechanism best seen on FIGS. 3, 5 and 6 for allowing the execution of resistive movement of the leg. More precisely, this mechanism allows the adjustment of different degrees of tension during extension and flexion of the leg. The resistance mechanism consists of a pair of pistons (30). Each piston (30) has an end connected to a portion of the side edge (24) of the leg support member (14) and an opposite end connected to a portion of the main frame (12). The best feature of this mechanism is to offer a linear type resistance during the complete range of movement, which is constant and unvariable like body weight in functional activity A blocking mechanism may also be provided for allowing instant pause of the extension and flexion of the leg and prevent reversal of movement direction when desired. The blocking mechanism comprises a ratchet wheel (31) and a rack (32). The ratchet (30) further comprises a first and second lever (34, 36). This system allows instant pause at different position of the leg.

Figure 9:
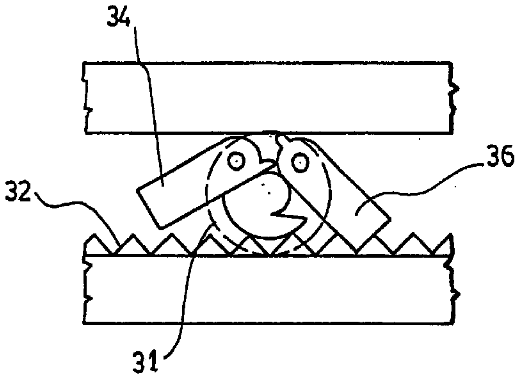
FIG. 9 is a side view of a blocking mechanism according to a preferred embodiment of the orthopedic apparatus of the present invention at a blocking position for the extension movement.

As shown in FIG. 9, for blocking the extension of the leg, the left lever (36) is disengaged, the right lever (34) is engaged.

Figure 10:
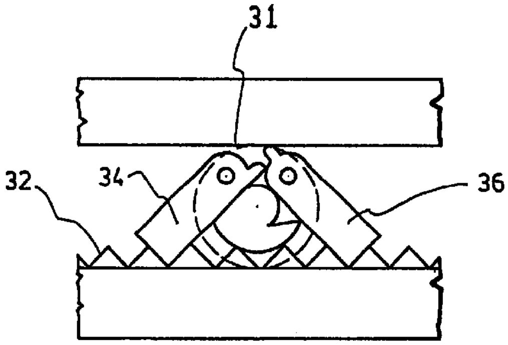
FIG. 10 is a side view of the blocking mechanism of FIG. 9 at a complete blocking position.

As shown in FIG. 10, for a complete block of the movement (extension or flexion), the ratchet wheel (31) is turned anticlockwise so that both levers (34, 36) are engaged in the rack (32).

Figure 11:
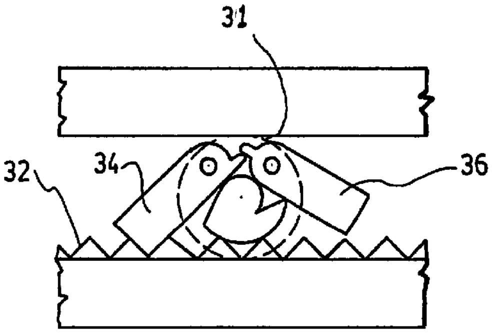
FIG. 11 is a side view of the blocking mechanism of FIG. 9 at a blocking position for the flexion movement.

When the ratchet wheel (31) is further rotated anticlockwise, the blocking mechanism attains a third position shown in FIG. 11. This is the blocking position for the flexion movement. At this position, the left lever (36) remains engaged in the rack and the right lever (34) is disengaged.

Figure 12:
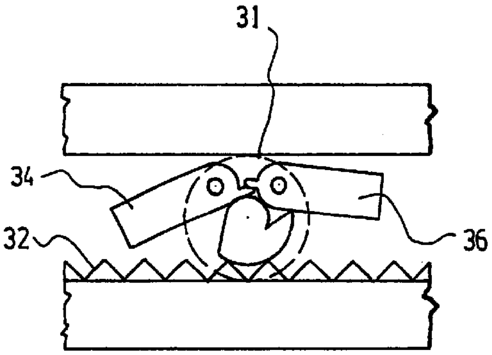
FIG. 12 is a side view of the blocking mechanism of FIG. 9 at a disengaged position.

Still turning anticlockwise, the right lever (34) tip over the left lever (36) thereby disengaging it from the rack (32). This position is the free position and is shown in FIG. 12.

Figure 8:
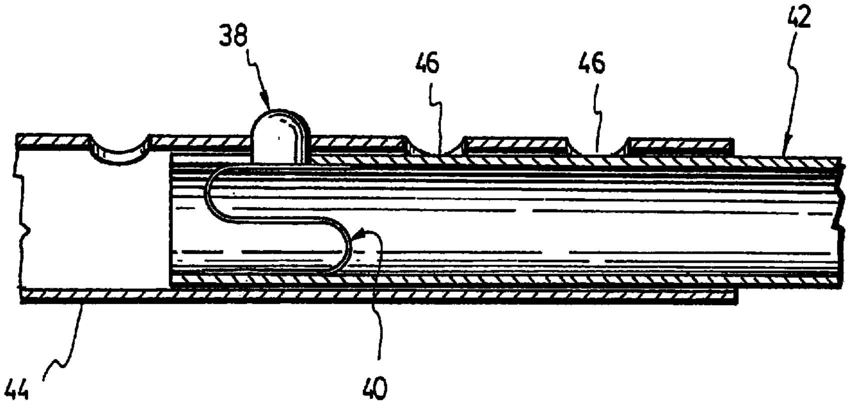
FIG. 8 is a longitudinal section view of a static adjustment mechanism according to a preferred embodiment of the orthopedic apparatus of the present invention.

As shown in FIG. 8, the orthopedic apparatus (10) may further be provided with a static adjustment mechanism for adjusting the first and second portions (18, 20) of the leg support member (14) to a predetermined length. The static adjustment mechanism may consist of a spring-knob (38, 40) on an internal tube (42) and a plurality of holes (46) at the corresponding end of the side edges (24, 26) of the first and second portions (18, 20). Hence to adjust the length of the exerciser (10), the user simply needs to push in the knob (38) downwards and pull the internal tube (42) in or out of the external tube (44) to the hole (46) corresponding to the desired position/length. Accordingly, the first and second portions 18, 20 are further provided with means 19, 21 (see FIGS. 3 and 4) to allow for this variation in length while all the same supporting the leg properly.

Another feature of the apparatus according to the invention is that it may include stoppers 51, 52 within each of the rails. These stoppers can be used to limit the range of motion of the leg during flexion and extension, so that the leg, instead of rotating between approximately 0° to 180°, can be made to rotate within a smaller range by bringing the stoppers closer together, either independently or together. As shown in FIG. 3, stopper 51 limits flexion and stopper 52 limits extension. The stoppers can be any type of mechanism which can be locked into place at the desired position along the rail, so that the stopper effectively stops the motion of the second and third portions of the apparatus along the rails and does not translate once it has been fixed in a predetermined position.

Preferably, stoppers 51 (one in each rail) and stoppers 52 (one in each rail) are moved simultaneously. To that effect, stoppers 51 could be mechanically connected together, and stoppers 52 could be mechanically connected together.

As can be appreciated, the orthopedic apparatus (10) according to the present invention provides a compact and portable exerciser that is easy to handle. This apparatus is as complete as going to a gymnasium. It allows the execution of a wide range of exercise in the comfort of the bed. Furthermore, it is easily adjustable to the patient's proportion, i.e. different patients will have thighs and shanks of different lengths. It is easy to use since all the functions are integrated in the apparatus and do not require additional assistance from a nurse or a helper.

Hence, the present apparatus is complete since it incorporates all the physiological principles that allow fast recovery of the knee without adding stress to the same. Specifically, the first and second axes of rotation are substantially coincident throughout the range of motion. Furthermore, the apparatus according to the invention allows the use of the same mechanical device (i.e. the pistons 30) to either assist active movement to gain range or to resist active movement to gain strength.

Although the present invention has been explained hereinabove by way of a preferred embodiment thereof, it should be pointed out that any modifications to this preferred embodiment within the scope of the present description is not deemed to alter or change the nature and scope of the present invention.

What is claimed is:

1. In an orthopedic apparatus for resistive extension and flexion of a user's leg the orthopedic apparatus comprising a main frame having a pair of rails, a leg support member having a first end fixedly secured on said main frame and a second end slidably mounted on said pair of rails of said main frame, said leg support member comprising a first portion designed to receive the user's thigh, a second portion designed to receive the user's shank and a third portion designed to receive the user's foot, said first and second portions each comprising two opposite side edges defining the width of said leg support member, said first and second portions further being pivotally connected to each other and forming a rotational axis for allowing flexion of the user's knee, wherein the improvement comprises a dynamic adjustment mechanism in the form of an indented hinge between the first and second portions for minimizing tension on the user's knee during extension or flexion of the user's leg, said mechanism allowing substantially no eccentricity between the user's knee and the rotational axis, said first and second portions being pivotally connected together so that when the user's leg is flexed and extended, the user's knee and the rotational axis are substantially coincident throughout the range of motion.

2. In an orthopedic apparatus according to claim 1, further comprising a resistance mechanism for allowing adjustment of different degrees of tension during extension and flexion of the leg.

3. In an orthopedic apparatus according to claim 2, comprising a blocking mechanism for allowing instant pause of the extension and flexion of the leg and prevent temporary undesired reversal of movement.

4. In an orthopedic apparatus according to claim 3, further comprising a static adjustment mechanism for adjusting said first and second sections to a predetermined length.

5. In an orthopedic apparatus according to claim 4, wherein said static adjustment mechanism comprises a pair of internal and external tubes, the internal tubes being adapted to fit and slide inside a pair of external tubes, said internal and external tubes forming said side edges of said first and second portion respectively.

6. In an orthopedic apparatus according to claim 5, wherein said static adjustment mechanism further comprises a spring-knob on one end of said internal tube and a plurality of holes at a corresponding end of said external tube of said first and second portions.

7. In an orthopedic apparatus according to claim 2, wherein said resistance mechanism comprises a pair of pistons, each of said pistons having a first end connected to a portion of said side edge of said leg support member and a second end connected to a portion of said main frame.

8. In an orthopedic apparatus according to claim 3, wherein said blocking mechanism comprises a ratchet wheel and a rack, said ratchet wheel having a first and a second lever.

9. In an orthopedic apparatus according to claim 1, wherein said pair of rails is further provided with adjustable stoppers in each rail for limiting the range of motion during flexion and extension.

* * * * *